US008862231B2

(12) United States Patent
Kirchner et al.

(10) Patent No.: US 8,862,231 B2
(45) Date of Patent: Oct. 14, 2014

(54) COMPARISON OF RIGHT-VENTRICULAR AND LEFT-VENTRICULAR CONTRACTION USING AN ACCELEROMETER IN AN ARTERY CLOSE TO THE HEART

(75) Inventors: Jens Kirchner, Erlangen (DE); Michael Vollkron, Pressbaum (AT); Olaf Skerl, Bad Doberan (DE)

(73) Assignee: Biotronik SE & Co. KG (DE)

( * ) Notice: Subject to any disclaimer, the term of this patent is extended or adjusted under 35 U.S.C. 154(b) by 0 days.

(21) Appl. No.: 13/587,997

(22) Filed: Aug. 17, 2012

(65) Prior Publication Data
US 2013/0053907 A1 Feb. 28, 2013

Related U.S. Application Data

(60) Provisional application No. 61/526,280, filed on Aug. 23, 2011.

(51) Int. Cl.
*A61N 1/00* (2006.01)
*A61B 5/11* (2006.01)
*A61B 5/00* (2006.01)

(52) U.S. Cl.
CPC .............. *A61B 5/1107* (2013.01); *A61B 5/686* (2013.01); *A61B 5/6869* (2013.01)
USPC .......................................................... 607/18

(58) Field of Classification Search
USPC ....................................... 607/4–28
See application file for complete search history.

(56) References Cited

U.S. PATENT DOCUMENTS

| 7,130,689 | B1 | 10/2006 | Turcott |
| 7,756,580 | B1 | 7/2010 | Turcott |
| 2005/0027320 | A1* | 2/2005 | Nehls et al. ........................ 607/9 |
| 2005/0209649 | A1 | 9/2005 | Ferek-petric |
| 2006/0009811 | A1* | 1/2006 | Sheldon et al. .................. 607/17 |
| 2006/0241335 | A1 | 10/2006 | Benkowski et al. |
| 2008/0195162 | A1 | 8/2008 | Lippert et al. |
| 2009/0005632 | A1 | 1/2009 | Schima et al. |
| 2009/0216145 | A1 | 8/2009 | Skerl et al. |
| 2010/0010354 | A1 | 1/2010 | Skerl et al. |
| 2010/0056888 | A1 | 3/2010 | Skerl et al. |
| 2010/0198284 | A1* | 8/2010 | Zhou et al. ........................ 607/4 |
| 2010/0241186 | A1 | 9/2010 | Turcott |
| 2010/0268041 | A1 | 10/2010 | Kraemer et al. |
| 2010/0268294 | A1 | 10/2010 | Vollkron et al. |
| 2011/0029035 | A1 | 2/2011 | Vollkron et al. |
| 2011/0112598 | A1 | 5/2011 | Vollkron et al. |
| 2011/0224520 | A1 | 9/2011 | Skerl et al. |
| 2011/0224527 | A1 | 9/2011 | Czygan et al. |
| 2011/0224748 | A1 | 9/2011 | Lippert et al. |

(Continued)

OTHER PUBLICATIONS

European Search Report, EP12179253, Nov. 23, 2012, 2 pgs.

*Primary Examiner* — Scott Getzow
(74) *Attorney, Agent, or Firm* — Craig A. Fieschko; DeWitt Ross & Stevens S.C.

(57) ABSTRACT

An implantable medical device includes a multi-axial acceleration sensor and an evaluation unit connected thereto. The evaluation unit is configured to (1) split the accelerometer output signal into at least two signal components, one of which is associated with a right-ventricular contraction and another of which is associated with a left-ventricular contraction; (2) detect events in the signal components, and/or determine signal features therein; and (3) determine at least one characteristic value K by evaluating the signal components, and/or the events and/or signal features therein.

25 Claims, 9 Drawing Sheets

(56) References Cited

U.S. PATENT DOCUMENTS

| | | |
|---|---|---|
| 2012/0035436 A1 | 2/2012 | Kirchner et al. |
| 2012/0035453 A1 | 2/2012 | Skerl et al. |
| 2012/0078318 A1 | 3/2012 | Kirchner et al. |
| 2012/0078342 A1 | 3/2012 | Vollkron et al. |

* cited by examiner

COMPARISON OF RIGHT-VENTRICULAR AND LEFT-VENTRICULAR CONTRACTION USING AN ACCELEROMETER IN AN ARTERY CLOSE TO THE HEART

CROSS-REFERENCE TO RELATED APPLICATIONS

This application claims priority under 35 USC §119(e) to U.S. Provisional Patent Application 61/526,280 filed 23 Aug. 2011, the entirety of which is incorporated by reference herein.

FIELD OF THE INVENTION

The invention relates to an implantable medical device including a multi-axial acceleration sensor, and an evaluation unit connected thereto which is designed to evaluate an accelerometer output signal of the acceleration sensor. Such devices are known, for example, in the form of implantable, rate-adaptive cardiac pacemakers, wherein an acceleration sensor is used to detect physical activity of a cardiac pacemaker patient.

BACKGROUND OF THE INVENTION

Current devices for the monitoring of cardiac functions and/or for the control of therapeutic devices provide limited options for monitoring and/or control. It would therefore be useful to have additional devices and monitoring and/or control techniques available which efficiently provide additional and/or alternative features. In particular, it would be useful to have additional devices and techniques allowing detection of pathological changes in ventricular contraction behavior, and allowing the monitoring of hemodynamics.

SUMMARY OF THE INVENTION

The invention involves an implantable medical device including a multi-axial accelerometer (acceleration sensor), and an evaluation unit connected thereto. The evaluation unit is configured to evaluate an accelerometer output signal by:
(1) extracting at least two signal components A1 and A2 from the accelerometer output signal, one of which is associated with a right-ventricular contraction of a heart, and one of which is associated with a left-ventricular contraction of a heart;
(2) determines, in the signal components A1 and A2, signal characteristics (events and/or features) such as peak amplitudes, intervals, frequencies, etc. This can be done, for example, by the evaluation unit applying suitable evaluation techniques to the two signal components;
(3) determines at least one characteristic value K by evaluating the signal components A1 and A2, and/or by evaluating the characteristics determined from the signal components.

The resulting device preferably includes:
(1) A 3D accelerometer which is implanted for use close to the heart in a suitable position in the pulmonary artery or the aorta, and is used to measure multi-axial acceleration and generate an accelerometer output signal A that reflects the multi-axial acceleration.
(2) An evaluation unit that carries out the following method:
(a) Split the accelerometer output signal A into at least two signal components, at least two of which are associated with the right-ventricular contraction and the left-ventricular contraction (signal components A1 and A2);
(b) Determine suitable characteristics from signals A1 and A2 (e.g., identify events and/or signal features such as peak amplitudes, intervals, frequencies, etc.); and
(c) Determine at least one characteristic value K by using at least the signal components A1 and A2 from the foregoing step (a), and/or the characteristics determined in step (b).

Preferably, K is the ratio of two amplitude values of A1 and A2, e.g. the maximum amplitudes within one cardiac cycle. It is also preferable that K reflect the time delay between two events from A1 and A2, such as a quantity related to the VV delay.

The device offers the advantage that both ventricles can be monitored using one acceleration sensor, and the information that is derived is specific for a respective half of the heart. This is a significant advantage over known solutions wherein the left heart and the right heart are compared using separate sensors (which may analyze, for example, impedance, blood pressure, heart sounds, ballistocardiogram, etc.). For example, the two halves of the heart are typically compared using two spatially separated sensors which are placed in the ventricles or the adjacent arteries. In contrast to a 1-sensor system, the energy demand, susceptibility to error, and stress for the physician and patient are markedly increased with such a 2-sensor system.

Prior single-sensor methods are typically limited to either the behavior of the entire heart (heart sounds, ballistocardiogram) or a part of the heart (impedance), or, if they are recorded within one ventricle/artery, to a single half of the heart (endocardial accelerations, blood pressure). The two halves of the heart cannot be compared with each other using this approach.

The device preferably uses an acceleration sensor in the form of a 3D accelerometer which is designed for placement in the pulmonary artery or the aorta close to the heart.

Furthermore, the evaluation unit is configured to determine the signal components on the basis of directional components of the accelerometer output signal.

The region of the pulmonary artery inside and slightly behind the *Truncus pulmonalis*, in particular the base of the *Arteria pulmonaris dextra*, is characterized by close proximity to the aorta. During a heart contraction, motion components from the left ventricle and the right ventricle are superposed at this location. These components can be recorded, separated, and compared using a 3D accelerometer. The quantities calculated as a result are used to detect and monitor ventricle-specific, pathological changes in contraction behavior.

Given that the anatomy of the aorta and the pulmonary artery differ, the directional components of the accelerations caused by blood pulsation, and the accelerometer output signal that reflects blood pulsation, differ between the aorta and the pulmonary artery. Moreover, a time delay occurs between these components due to the typical delay between the contractions of the left ventricle and the right ventricle. These two effects enable the evaluation unit to separate acceleration components from the aorta and the pulmonary artery.

In addition, the evaluation unit is preferably configured to determine the characteristic value K on the basis of the ratio of two amplitude values, in particular on the basis of the ratio of maximum amplitudes within one cardiac cycle. Alternatively or additionally, the evaluation unit can be configured to determine the characteristic value K on the basis of a time delay between two corresponding events in the (two or more) signal components. A characteristic value K that correlates with an interventricular delay time (VV delay) is particularly preferred.

The evaluation unit is also preferably configured to derive at least one more signal component A3 in the foregoing step (a), and to determine the characteristic value K as a function of one of the values of the characteristics derived from signal component A3. Signal component A3 is preferably a signal component that reflects the activity of the patient, and the value derived therefrom preferably reflects the patient's mean activity during a predefined time interval. Certain ranges of the activity signal can be combined to form activity levels. Alternatively or additionally, the evaluation unit can be configured to also derive at least one more signal component A3 in step (a) on the basis of the accelerometer output signal, and to determine the characteristic value K (only) at such points in time in which a quantity derived from signal component A3 lies in a predefined value range.

Furthermore, the evaluation unit can be configured to also determine a quantity J on the basis of signal components A1 and/or A2—e.g., a heart rate of a patient—and determine characteristic value K as a function of quantity J. In this case as well, the evaluation unit can be configured to determine quantity J on the basis of signal components A1 and/or A2, and to define characteristic value K (only) at such points in time in which J lies in a predefined value range.

The implantable device is also preferably equipped with a further sensor for measuring another signal B, and the evaluation unit is configured to determine quantity K as a function of a quantity derived from signal B. This additional sensor is preferably a blood pressure sensor and/or impedance sensor, such that signal B reflects blood pressure or impedance. The quantity derived from signal B preferably corresponds to a mean, a diastolic value, or a systolic value. Additionally or alternatively, the implantable device include a further sensor for measuring additional signal B, and the evaluation unit can be configured to determine quantity K at such points in time at which a quantity derived from signal B lies in a predefined value range.

In a preferred version of the invention, the device is configured to determine characteristic values of respiration, in particular frequency and amplitude. The device might determine the degree of shortness of breath at a given physical load, and/or it might detect sleep apnea.

In preferred versions, the implantable device is also configured to measure a sensor quantity that correlates with the electrical stimulation of the heart, and to derive a quantity that is associated with the electromechanical coupling.

Preferably, the implantable device includes a control unit which is configured to use quantity K to detect arrhythmias, and to control therapy units (e.g., cardiac electrical stimulation units) of the implantable medical device accordingly. Quantity K is preferably used as a shock criterion for defibrillators, as a trigger for antitachycardia pacing, or purely as a monitoring quantity (as by reflecting the number and duration of certain tachycardias).

The implantable device may also be configured to utilize quantity K to monitor the hemodynamics of a patient and, in particular, to detect the occurrence and worsening of cardiac diseases such as cardiac insufficiency (CHF). The quantity K, and/or conditions derived therefrom, may be integrated into an algorithm for the prediction of cardiac decompensation; into the display in an external monitoring system for the treating physician; and/or into the generation of an alarm when a threshold value has been exceeded.

The implantable device may also be configured to utilize quantity K to monitor the effect of a drug and the patient's taking of the drug.

The implantable device preferably includes a control unit which is configured to adjust settings of the implantable medical device depending on the characteristic value K. For example, the control unit may adjust pacing parameters in a pacemaker/defibrillator (e.g. AV/VV delay), or might dosage adjustment in the case of automatic drug delivery, in dependence on K.

The implantable device is beneficially provided in the form of a cardiac stimulator, in particular a biventricular cardiac pacemaker or defibrillator/cardioverter.

BRIEF DESCRIPTION OF THE DRAWINGS

The invention will now be explained in greater detail with reference to the accompanying figures, which show.

DETAILED DESCRIPTION OF EXEMPLARY VERSIONS OF THE INVENTION

Figure 1:
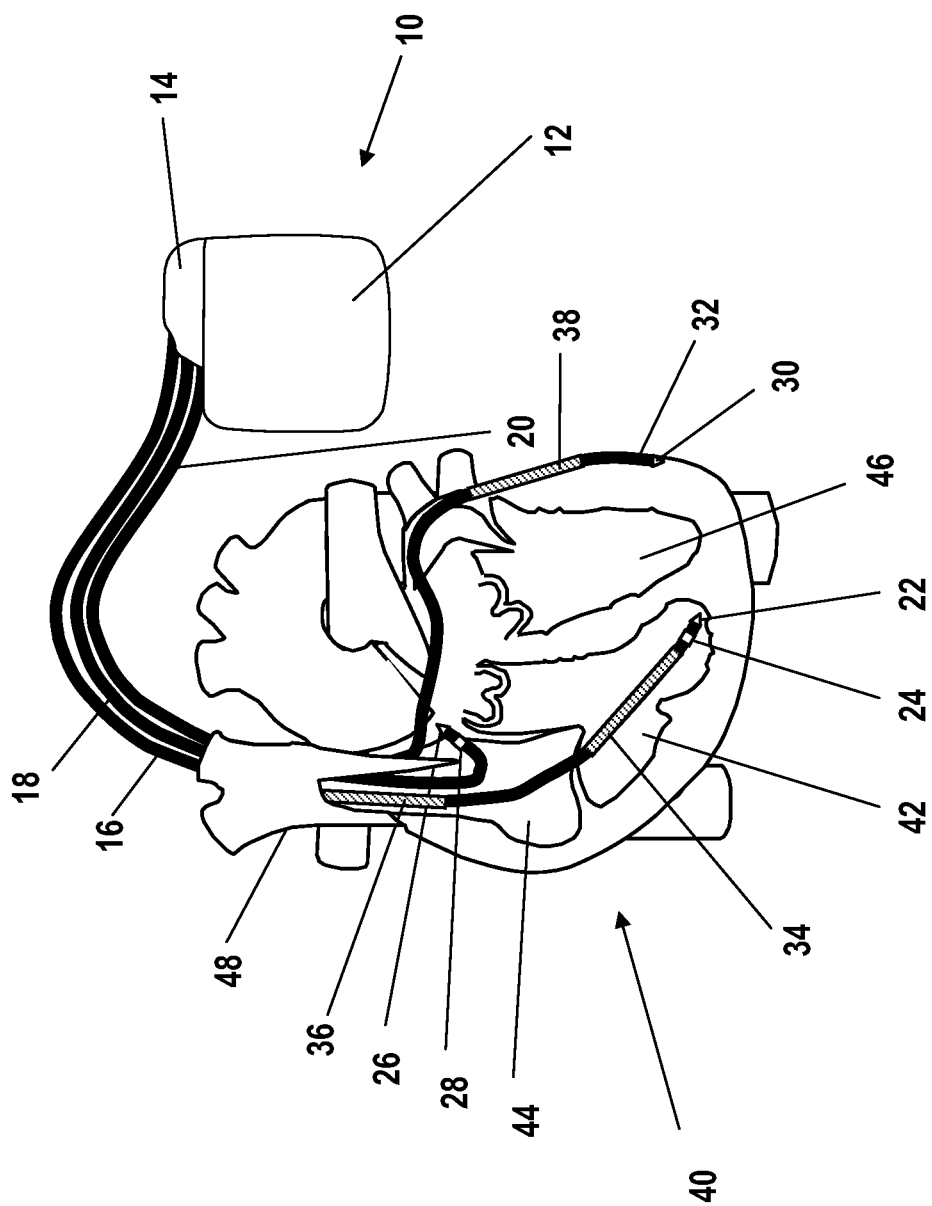
FIG. 1: an implantable medical device (implantable cardiac stimulator) and implantable electrode leads connected thereto.

FIG. 1 shows an exemplary heart monitor in the form of an implantable medical device, specifically in the form of an implantable cardiac stimulator 10. Cardiac stimulator 10 is designed as a biventricular cardiac pacemaker and cardioverter/defibrillator.

Cardiac stimulator 10 includes a housing 12 composed of metal, which can also serve as a large surface-area electrode. A "header" 14 made of plastic is attached to housing 12, which, as a connector housing including plug boxes, can accommodate plugs of electrode leads, in order to thereby electrically connect electrodes on the electrode leads to electrical components in the interior of housing 12.

In the case shown, a total of three electrode leads are connected to cardiac pacemaker 10, specifically a right-ventricular electrode lead 16, a right-atrial electrode lead 18, and a left-ventricular electrode lead 20. Each of these electrode leads carries, on the distal end thereof, a pair of relatively small surface-area stimulation and sensing electrodes, including a right-ventricular tip electrode RV-TIP 22, a right-ventricular ring electrode RV-RING 24, a right-atrial tip electrode RA-TIP 26, a right-atrial ring electrode RA-TIP 28, a right-atrial electrode lead 18 and, finally, a left-ventricular tip electrode RV-TIP 30 and a left-ventricular ring electrode RV-TIP 32 on the distal end of left-ventricular electrode lead 20.

Electrodes are also provided for the purpose of delivering a defibrillation shock, each of which is in the form of a relatively large surface-area defibrillation shock coil. These include a right-ventricular shock electrode RV-COIL 34, which is disposed on right-ventricular electrode lead 16 in the vicinity of the distal end thereof. Right-ventricular electrode lead 16 also carries a proximal shock electrode VC-COIL 36 which is provided for placement in the vena cava. A left-ventricular shock electrode RV-COIL 38 is also provided in the vicinity of the distal end of left-ventricular electrode lead 20.

FIG. 1 presents a schematic depiction of how the individual electrodes are approximately situated in the heart after implantation. For instance, FIG. 1 shows a schematic depiction of a heart 40 with right ventricle 42 thereof, right atrium 44 thereof, and left ventricle 46 thereof. A section of vena cava superior 48 is also shown.

Figure 2:
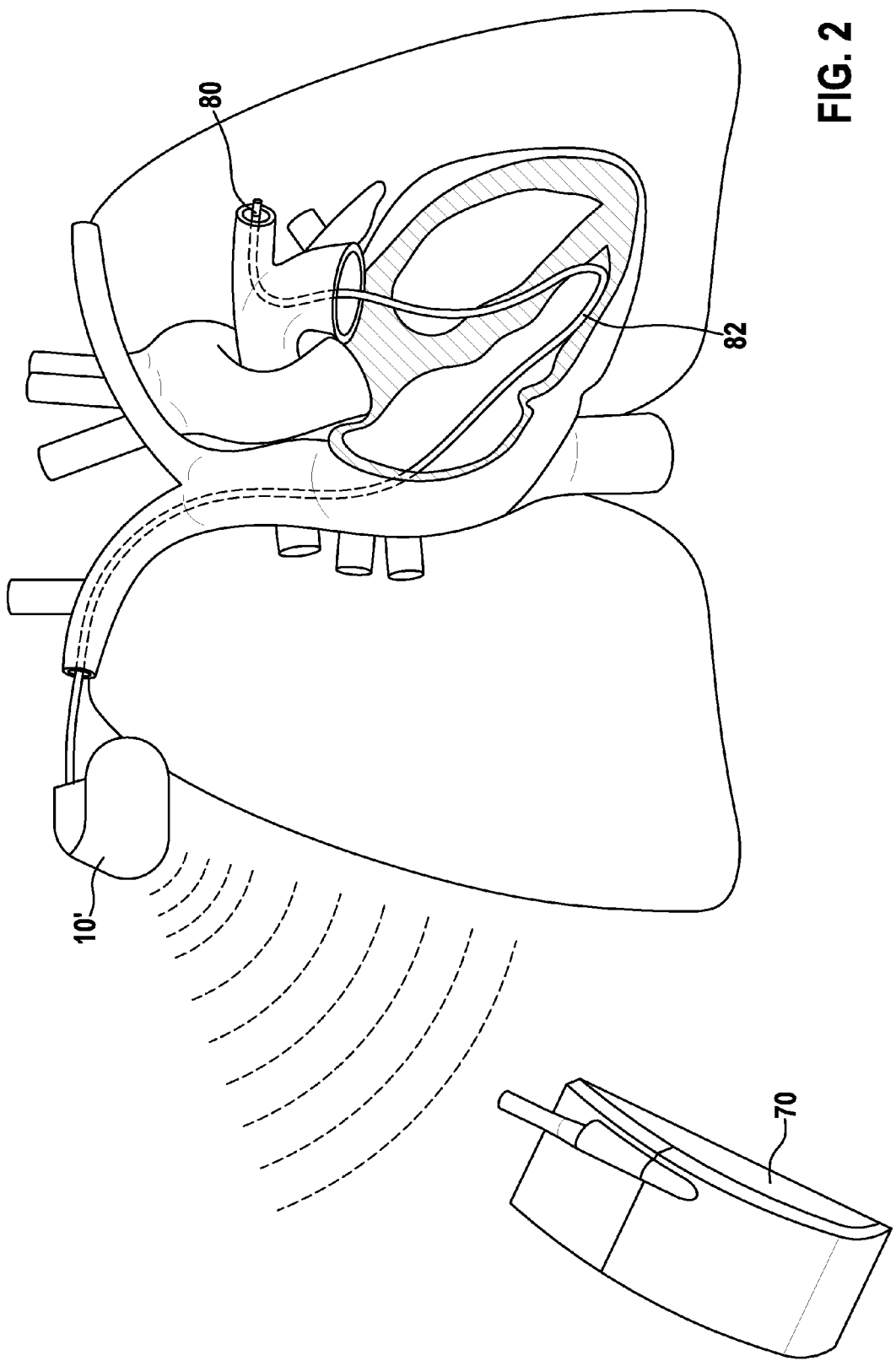
FIG. 2: an implantable medical device (heart monitor) with a multi-axial acceleration sensor connected thereto and placed in the pulmonary artery.

FIG. 2 shows an implantable medical device 10' provided in the form of a heart monitor. For simplicity, the electrode leads depicted in FIG. 1 have been omitted from the illustration. In place thereof, an external device 70 (patient device) is shown, which is used for wireless communication with implantable medical device 10'. FIG. 2 also specifically an acceleration sensor unit 80 which is designed as a multi-axial acceleration sensor and is connected via a connecting lead 82 to implantable medical device 10'. Acceleration sensor unit 80 is disposed close to the heart in the pulmonary artery, in order to record multi-axial accelerations there and deliver a related accelerometer output signal.

Figure 3:
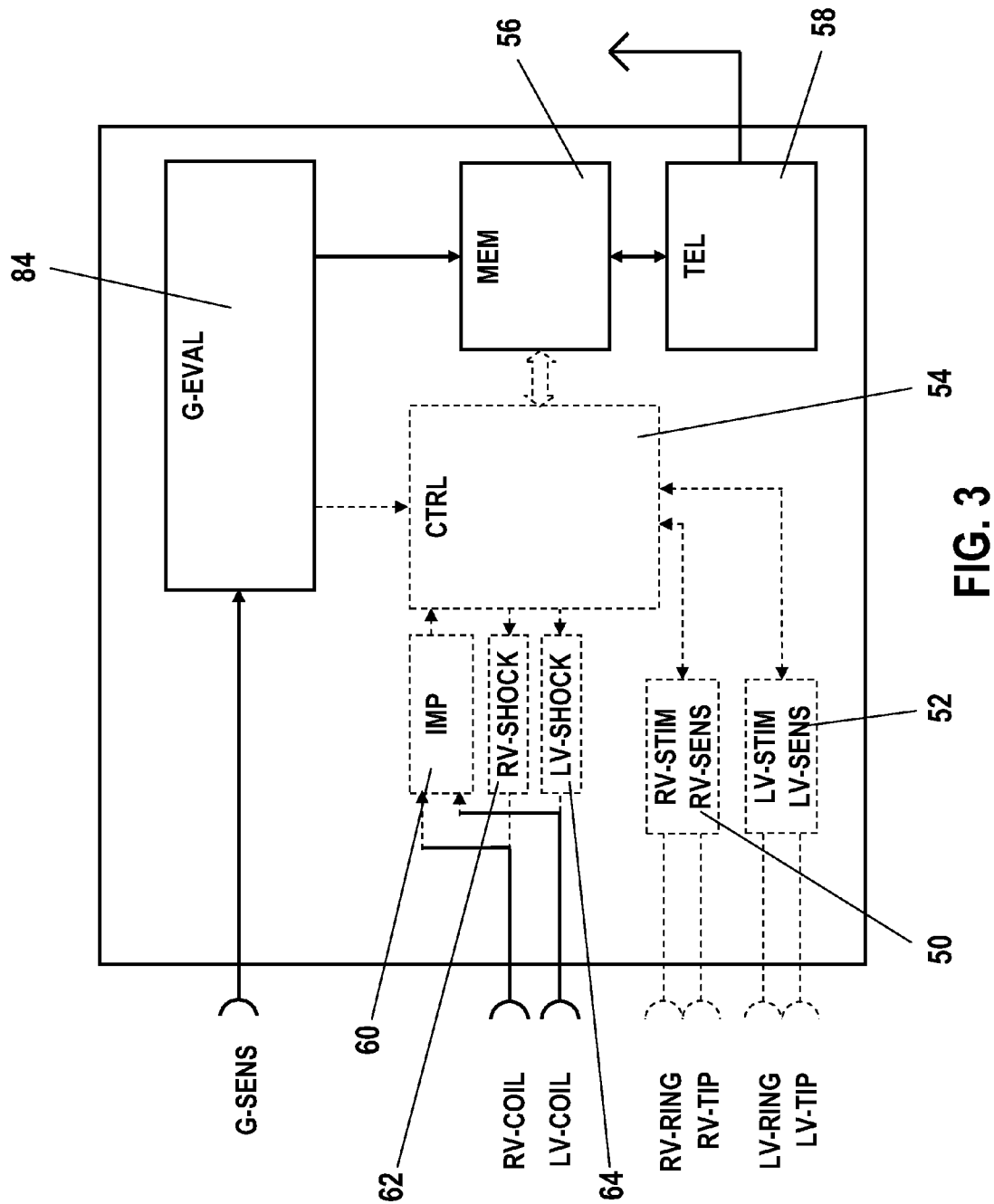
FIG. 3: shows, as examples, a few components of an implantable medical device of the type depicted in FIG. 1 or 2.

FIG. 3 shows a few of the electrical and electronic components within the housing 12 of the cardiac stimulator 10 of FIG. 1, specifically a right-ventricular stimulation unit RV-STIM and a right-ventricular sensing unit RV-SENS, which are depicted schematically and are labeled with the same reference character 50. The right-ventricular stimulation unit and the right-ventricular sensing unit are connected to the electrical connector for right-ventricular ring electrode RV-RING and right-ventricular tip electrode RV-TIP. In the same manner, a left-ventricular stimulation unit LV-STIM and a left-ventricular sensing unit LV-SENS (both labeled with reference character 52) are connected to the electrical connector for left-ventricular tip electrode LV-TIP and left-ventricular ring electrode LV-RING. The stimulation and sensing units are also connected to a central control unit CTRL 54.

The control unit is also connected to an impedance sensor 60 which is also connected to the connectors RV-Coil and LV-Coil in order to deliver a sub-threshold, pulsed, bipolar measuring current via shock electrodes 34 and 36, and to thereby measure the voltage drop across the two shock electrodes 34 and 36, and thereby determine impedance.

Control unit CTRL 54 is connected to a memory MEM 56 which, in turn, is connected to a telemetry unit TEL 58. Memory unit MEM 56 is used to temporarily store physiological data or operational data detected by cardiac stimulator 10 when they should be transmitted via telemetry TEL 58 to an external device. In addition, parameters or program data can be stored in memory unit MEM 56, which are accessed by control unit CTRL 54 and influence the operation of cardiac stimulator 10.

FIG. 3 also shows that, for the case in which cardiac stimulator 10 is a defibrillator, it is also possible to provide a right-ventricular shock generator RV-SHOCK 62 and a left-ventricular shock generator LV-SHOCK 64, each of which can be connected to an electrical connector RV-COIL for the right-ventricular shock electrode, and to a connector LV-COIL for the left-ventricular shock electrode, and to control unit CTRL 54.

Stimulation units 50 and 52, and shock generators 62 and 64, are therapy units of the implantable medical device which are controlled by control unit 54. The delivery of stimulation pulses to one or more ventricles on-demand and in a rate-adapted manner, and the delivery of cardioversion pulses or defibrillation shocks in the case of tachycardias or fibrillations, can be controlled by control unit 54 in a known manner. Such therapies can be optimized further by control unit 54, however, in that control unit 54 controls these therapies depending on the accelerometer output signal from acceleration sensor 80 and/or signal components and quantities derived from the accelerometer output signal by an acceleration evaluation unit 84.

Memory MEM 56 is connected on the output side to telemetry unit TEL 58, which is designed such that the values stored in memory 56 are transmitted by telemetry unit 58 using a transmission assigned to telemetry unit 58 at a transmission point in time that repeats at regular intervals, in such a way that the values are received by an external device 96 and can be forwarded to (for example) a service center, a physician, or the like.

Control unit 54 is also connected to a 3D acceleration sensor (3D accelerometer) which includes external acceleration sensor unit 80 (see FIG. 2) designed for positioning in the pulmonary artery in order to detect multi-axial accelerations there. External acceleration sensor unit 80 is connected via connecting lead 82 to acceleration evaluation unit 84, whereby these components can collectively be regarded as representing the 3D acceleration sensor (the 3D accelerometer). In addition, the 3D acceleration sensor 80 (and 84) can be configured to detect dynamic accelerations, such as physical activity, or to detect a particular position of the device that corresponds to a particular position of the body given the implanted state of the device.

Acceleration evaluation unit 84 is configured to evaluate accelerometer output signals which reflect multi-axial accelerations and are detected by acceleration sensor unit 80 in the region of the pulmonary artery, as explained further below.

Figure 4:
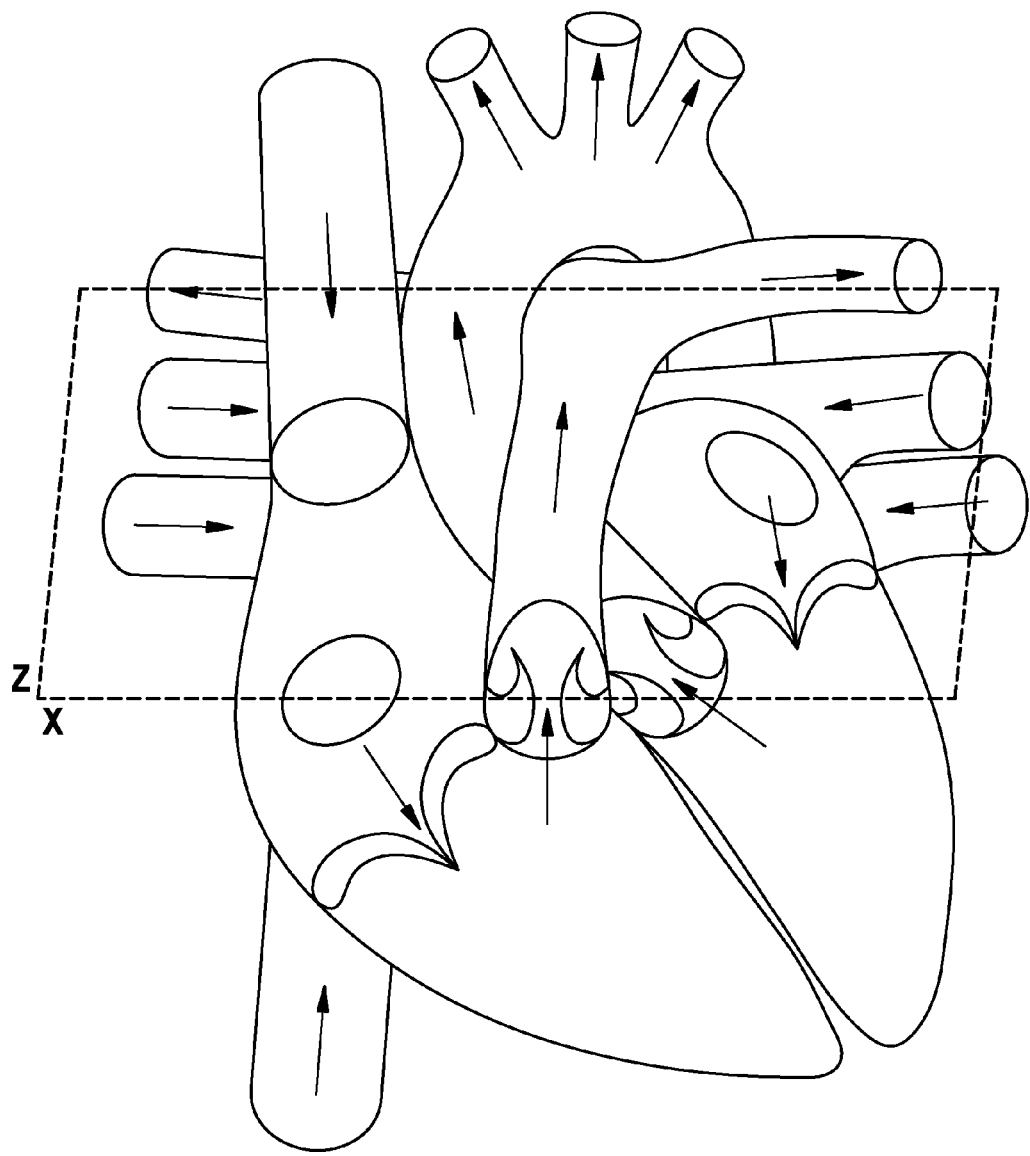
FIG. 4: shows the anatomy of the heart with adjacent blood vessels, and the direction of blood flow. The figure also indicates the plane in which the *Truncus pulmonalis* and the pulmonary arteries are situated.
Figure 6:
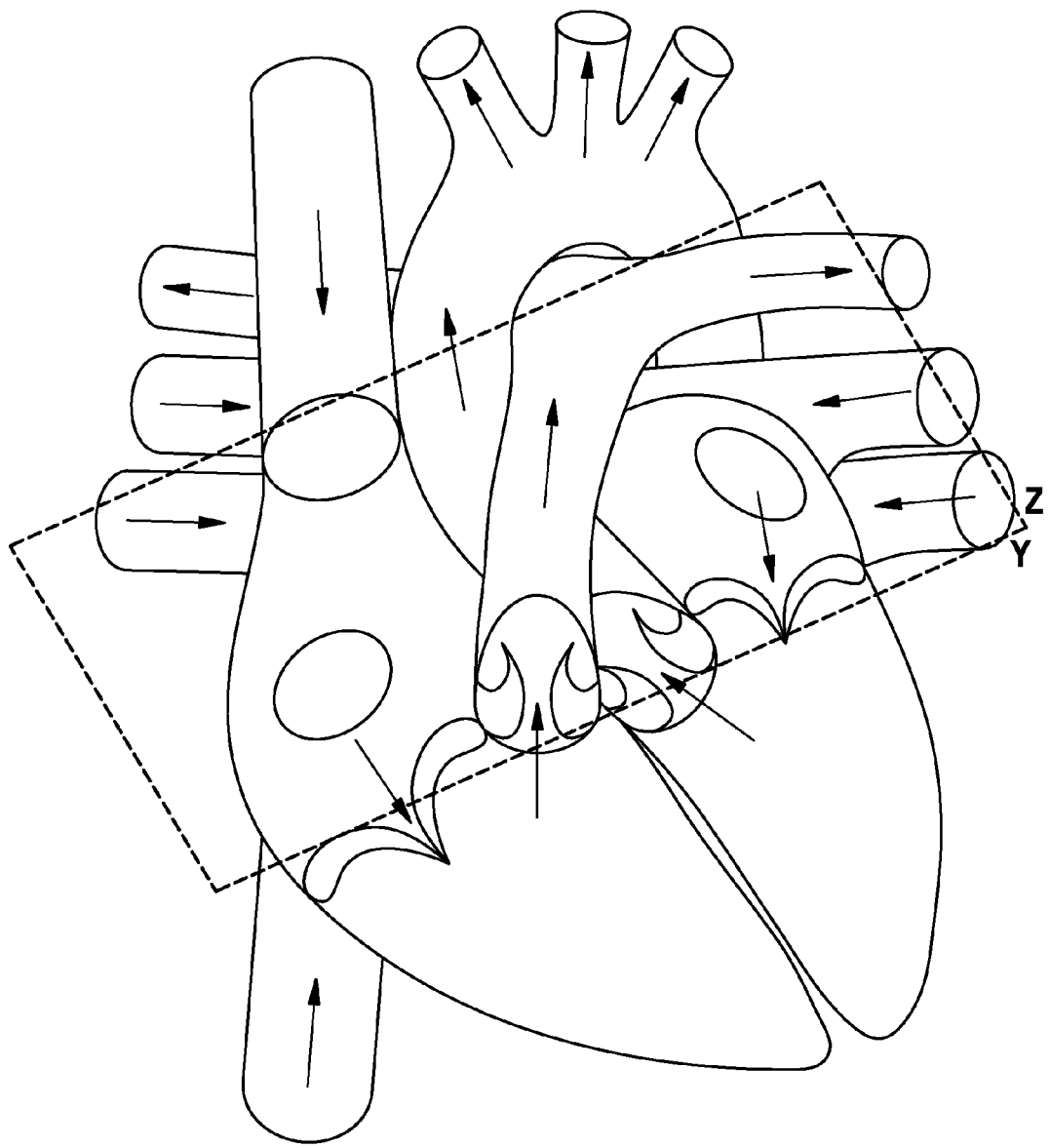
FIG. 6: shows the anatomy of the heart with adjacent blood vessels, and the direction of blood flow. The figure also indicates the plane in which the aorta is situated.
Figure 9:
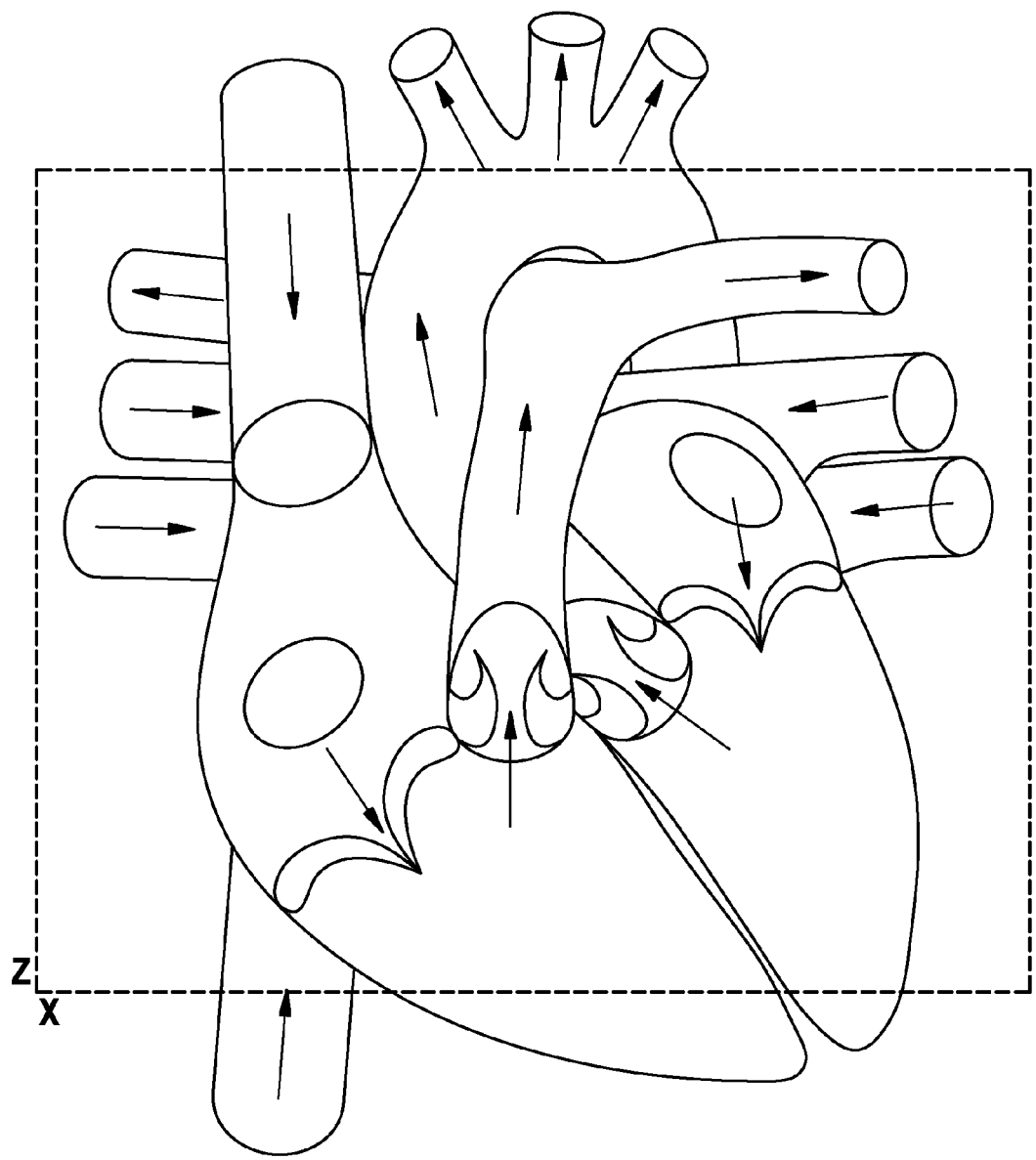
FIG. 9: shows the anatomy of the heart with adjacent blood vessels, and the direction of blood flow. The figure also indicates the plane along gravitation, in which the pulmonary arteries are situated.

FIGS. 4, 6 and 9 show how the pulmonary artery (PA) lies side-by-side with the aorta (Ao) in the region of the branching of the *Truncus pulmonalis* into the two pulmonary arteries. Movements of these vessels, and heart sounds that follow the pulsatile blood flow out of the ventricles are also transmitted here to the respective other vessel. These signals are recorded by 3D accelerometer 80. Preferably, external sensor unit 80 is placed in the pulmonary artery since the influence of the aorta in the pulmonary artery can be detected more clearly than the influence of the pulmonary artery in the aorta.

Figure 5:
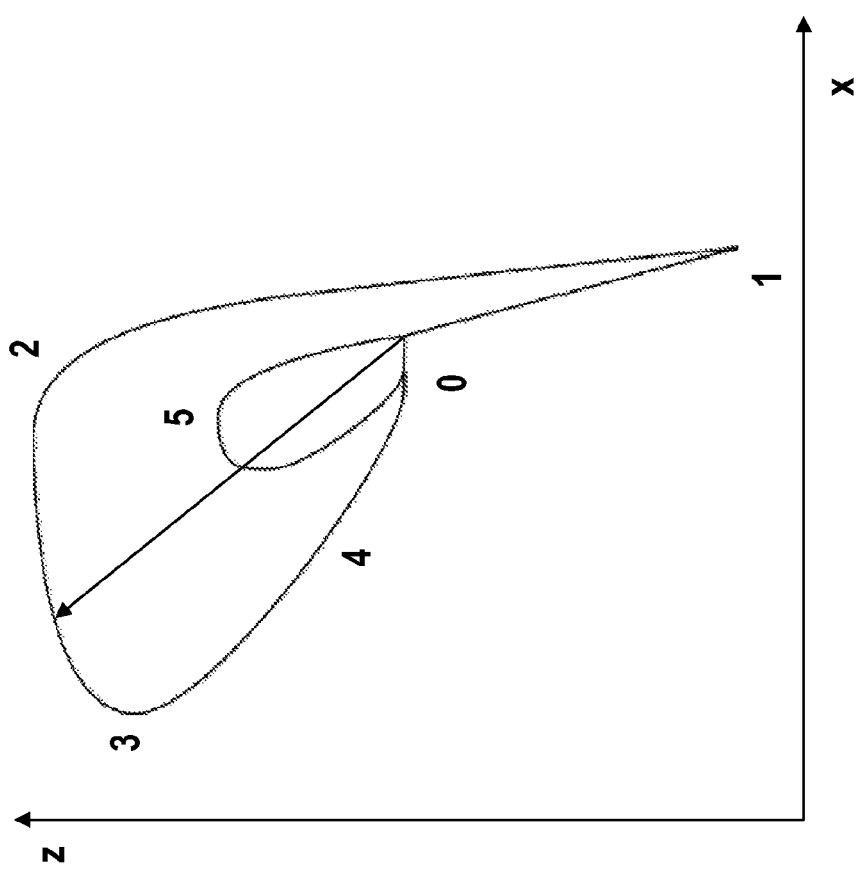
FIG. 5: shows the expected behavior of the accelerometer signal in the cutting plane through the *Truncus pulmonalis* and the *Arteria pulmonaris dextra* (see FIG. 4)
Figure 7:
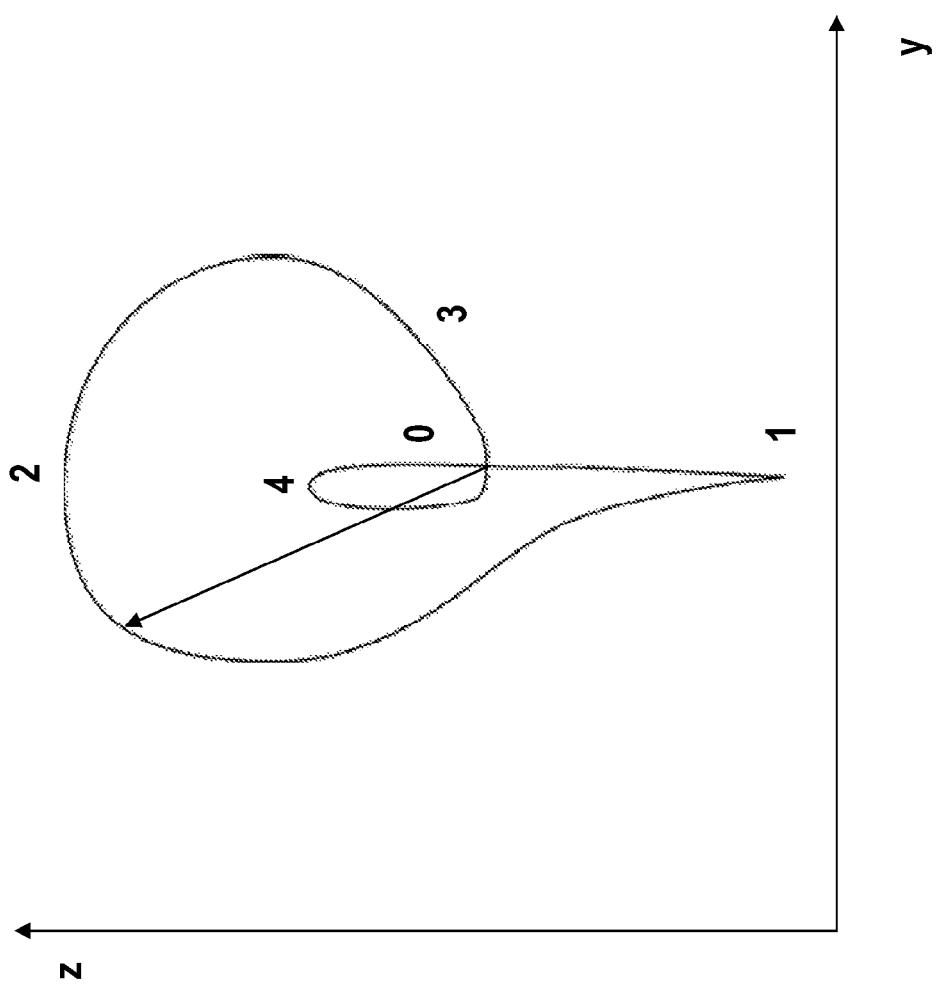
FIG. 7: shows the expected behavior of the accelerometer signal in the cutting plane through the aortic arch (see FIG. 6). This plane is approximately perpendicular to the plane in FIG. 4.
Figure 8:
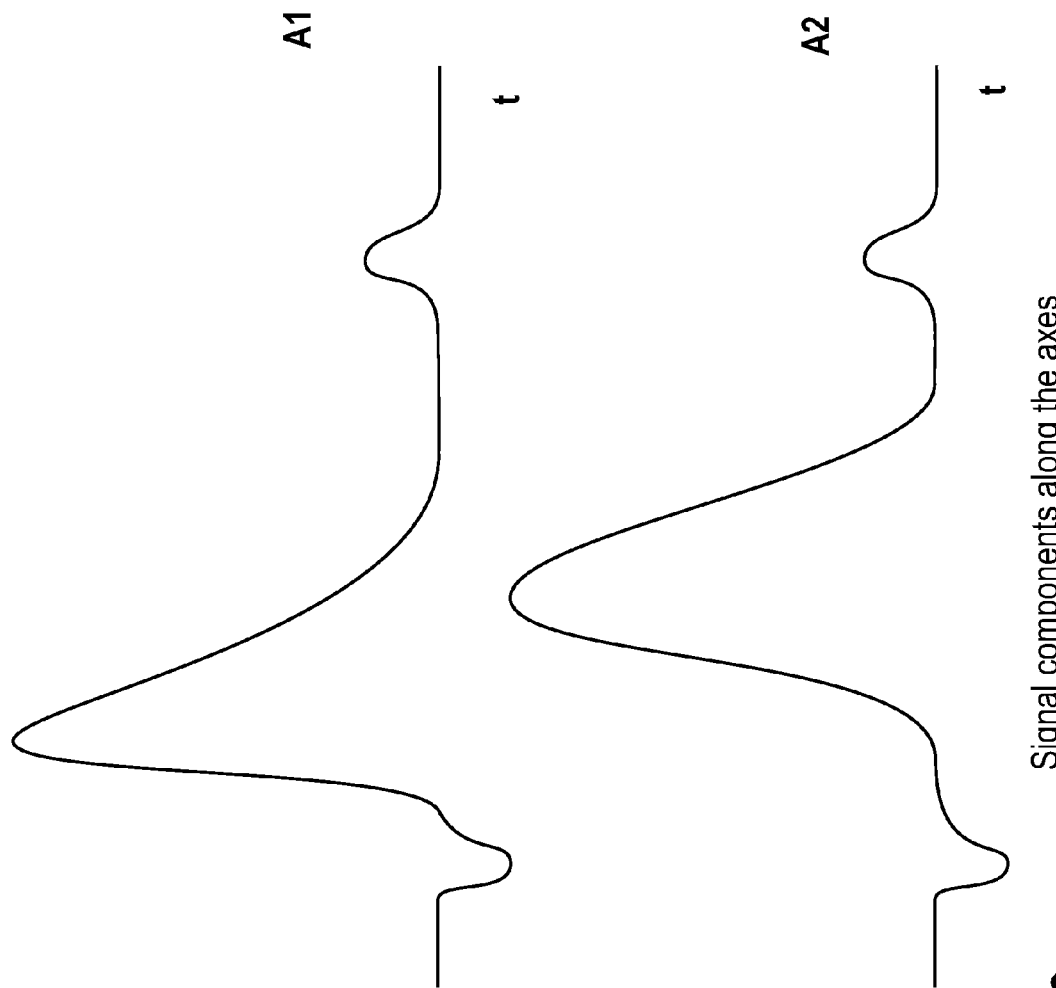
FIG. 8: shows the expected signal components of a multi-axial accelerometer output signal as a function of time, wherein the signal components result from the expected behavior of the acceleration signal in the direction of the x-axis and the y-axis in accordance with FIGS. 5 and 7. The upper signal corresponds to the right-ventricular contraction, and the lower signal corresponds to the left-ventricular contraction.

FIGS. 5 and 7 show the expected directional components of the accelerometer output signal caused by the blood pulsation. FIG. 8 shows the resulting behavior of the acceleration signal in the direction of the x-axis and y-axis in accordance with FIGS. 4 and 6. Upper signal A1 corresponds to the right-ventricular contraction, and lower signal A2 corresponds to the left-ventricular contraction. FIG. 9 shows the influence of gravitation on the accelerometer output signal.

Given that the anatomy of the aorta and the pulmonary artery differ, the directional components of the accelerometer output signals caused by blood pulsation are different. Moreover, a time delay occurs between these components due to the typical delay between the contractions of the left ventricle and the right ventricle. These two effects enable acceleration components from the aorta and the pulmonary artery to be separated.

The expected signal components are described in the following with reference to the schematic depictions in FIGS. 4 to 9. The following superposed components are expected in the accelerometer signal during one cardiac cycle.

First, the pumping mechanism of the heart and the resulting blood flow will be explained. The three-dimensional signal generated by the heart contracting and relaxing, and the blood flow, can be subdivided into two components, specifically:

(1) a first signal component that corresponds to the right-ventricular contraction and extends in the plane defined by the right-ventricular outflow passage and the right pulmonary artery (see FIG. 4); and (2) a second signal component that originates from the contraction of the left ventricle and extends in the plane in which the aortic arch lies (see FIG. 6).

The z-axes approximately coincide, and the x-axis and the y-axis are approximately perpendicular to one another.

The course of the acceleration vector over time depicted in FIG. 5 is caused by the contraction of the right ventricle. Starting in resting position 0, upon contraction of the right ventricle, the entire region of the heart base, including the arteries, is drawn in the direction of the apex of the heart (1). As a result, blood flows out of the ventricle, into the *Truncus pulmonalis*, and strikes the branching of the two pulmonary arteries (2). The blood pressure pulse reaches the right pulmonary artery, thereby accelerating the accelerometer along the axis of the PA (3). The heart begins to relax, and the accelerometer signal returns to the origin (4). When the ventricle relaxes, the valve plane rises in the direction of the heart base once more, thereby pressing the PA away from the apex of the heart (5).

The course of the acceleration vector over time depicted in FIG. 7 is caused by the contraction of the left ventricle. Starting in resting position 0, upon contraction of the left ventricle, the region of the heart base, including the aorta, is drawn in the direction of the apex of the heart (1). As a result, blood flows into the aortic arch; the accelerometer follows the wave front and describes an arch (2) until it returns to the resting position 0 (3). When the ventricle relaxes, the valve plane rises in the direction of the heart base once more, thereby pressing the aorta away from the apex of the heart (4).

The components along the x-axis and the y-axis could appear as depicted in FIG. 8. The slight break at the beginning of the cycle (1) arises from the movement of the valve plane and should take place synchronously in the two signals. The same applies for relaxation which results in a wave at the end of the cycle (5 and 4). The expulsion begins in the right ventricle (2 and 3) somewhat sooner than in the left ventricle (2), due to the lower counterpressure. Due to the shape of the aortic arch and the damping (when the accelerometer has been placed in the pulmonary artery), the acceleration peak that corresponds to the left ventricular contraction (lower signal) should be wider than that of the right ventricular contraction.

Now the influence of gravitation will be described; see FIG. 9. Gravitation is incorporated into the accelerometer signal as a time-constant component. This component can be used to calibrate the orientation of the accelerometer in three dimensions and, if the patient's position is known (prone/standing), to calibrate the orientation of the accelerometer in the body. This is required, for instance, when the direction of a peak is used as the criterion for assigning one of the signal components A1 or A2. Calibration is difficult in the presence of strong disturbing influences, e.g. when the patient is engaged in strenuous physical activity; methods in which calibration is unavoidable may have to be limited to times in which interferences are minimal, such as at night.

Now the potential disturbing influences will be discussed. Disturbing influences arise from device sounds, physical activity of the patient, or movements outside of the body (bus/train/car, elevator, escalator, etc.). Appearance, amplitude, and spatial orientation depend upon the causes. Device sounds represent white noise that is identical in all spatial directions. Accelerometer signals caused by vibrations due to transportation means will be similar, although spatially oriented in the direction of gravitation, and possibly with a few more strongly pronounced frequency ranges. Directional changes, start-up and braking (when driving a car, in elevators, or on escalators) appear as temporary directed peaks.

The use of the accelerometer output signal will now be discussed. Diagnostic indices can be determined on the basis of the individual components of the accelerometer output signal: amplitudes at selected points in time, time differences between selected events, etc. In particular, it is expected that the amplitude of the particular acceleration component is proportional to the contractility of the particular ventricle; the AV delay can be determined on the basis of suitable features of the left ventricular component and the right ventricular component. Acceleration evaluation unit 84 is preferably configured to determine the signal components, and to derive further quantities therefrom and, in particular, the stated diagnostic indices.

As an extension of the foregoing concepts, acceleration evaluation unit 84 can also be configured to evaluate the diagnostic indices depending on the patient's activity. To this end, the acceleration evaluation unit extracts the signal component that represents the activity from the accelerometer signal. Thus, for example, monitoring and/or treatment can be initiated when certain measured or calculated conditions arise in the right and/or left ventricles, and when the patient's activity falls within a certain window.

In the same manner, the acceleration evaluation unit can evaluate the indices depending on the heart rate that the acceleration evaluation unit 84 likewise determines from the accelerometer output signal using known methods.

The sensor system described can be combined with other sensors, thereby enabling the indices described to also be evaluated depending on other quantities, such as blood pressure or impedance signals.

The monitoring functionality of the invention is supplemented by the separate determination of the valve opening and closing times. Changes in the characteristic signal behaviors can indicate the development/presence of constrictions or leaks at the inflow/outflow flaps of the two ventricles.

In addition, the dynamic expansion of the aorta is detected indirectly during the systole on the left side. It is therefore possible to obtain quantitative deductions of the elasticity of the aorta. In this case as well, pathological changes (aneurysm, stenosis, arteriosclerosis) can be detected by analyzing the accelerometer output signal.

Structural changes in the ventricle are detected and quantified by separate analysis of the change in the length and rotational motion that the ventricle undergoes during the systole.

Pronounced paradoxical septum motions can be isolated in the accelerometer output signal by performing filtering accordingly.

Moreover, respiration can be monitored: the rise and fall of the diaphragm is extracted as a low-frequency signal from the accelerometer output signal. Furthermore, due to respiration, the volume distribution in the thorax fluctuates, as does the orientation of the heart, thereby making it possible to reconstruct a respiratory signal.

A further application is the hemodynamic characterization of arrhythmias, inter alia, as an additional criterion for the triggering of a defibrillation shock.

The system can also be used as a hemodynamic sensor, in that acceleration evaluation unit 84 determines suitable parameters from signal components A1 and A2 that describe the performance of the heart. These hemodynamic parameters can be used to monitor cardiac insufficiency or to optimize therapy parameters (e.g. AV delay, VV delay).

By also using other signals which (for example) describe the electrical activity of the heart, and which can be obtained using appropriate sensing units (e.g., IEGM, EKG), the acceleration evaluation unit can determine parameters that describe the electrical-mechanical coupling. These parameters can also be used to monitor the course of a disease or to optimize therapy.

The system requires only a single sensor in order to measure the contraction behavior of the heart, and to distinguish between the function of the left ventricle and the right ventricle, and to compare them. It can therefore accomplish more than sensors that are placed in other locations in the body. Compared to a 2-sensor system, the energy demand, susceptibility to error, and stress for the physician and patient are greatly reduced.

An acceleration sensor in the direct vicinity of the heart offers additional monitoring options. The technology could be used for patients with pacemakers/ICD and for HF patients who do not have such implants (e.g., patients who only have monitoring implants, rather than therapeutic implants).

In addition to integration of the measured indices in prediction algorithms or for adaptation of delivered therapies, it is also possible to derive characteristic values and detect/monitor diseases known to medically trained personnel (relationship of contractilities, respiratory parameters, delay times between the left ventricle and right ventricle, etc; arrhythmias, valve defects, contractility losses, paradoxial septal movements, etc.).

It will be apparent to those skilled in the art that numerous modifications and variations of the foregoing exemplary devices and techniques are possible in light of the foregoing discussion. The disclosed examples are presented for purposes of illustration only. Other alternate versions of the invention may include some or all of the features disclosed herein.

The invention is not intended to be limited to the preferred versions of the invention described above, but rather is intended to be limited only by the claims set out below. Thus, the invention encompasses all different versions that fall literally or equivalently within the scope of these claims.

What is claimed is:

1. An implantable medical device including:
    a. a multi-axial acceleration sensor configured to generate an accelerometer output signal, and
    b. an evaluation unit connected thereto, wherein the evaluation unit is configured to:
        (1) define at least two signal components A1 and A2 from the accelerometer output signal, wherein:
            i. the signal component A1 is associated with a right-ventricular contraction of a heart, and
            ii. the signal component A2 is associated with a left-ventricular contraction of the heart;
        (2) determine signal characteristics of each of the signal components A1 and A2, wherein the signal characteristics include amplitudes occurring within one cardiac cycle; and
        (3) define a characteristic value K from the signal characteristics, wherein the characteristic value K is a ratio of values of the amplitudes.

2. The implantable medical device of claim 1 wherein the implantable medical device is configured to deliver therapy to the heart in dependence on the characteristic value K.

3. The implantable medical device of claim 1 wherein the evaluation unit is configured to define the signal components A1 and A2 in accordance with directional components of the accelerometer output signal.

4. The implantable medical device of claim 1 wherein the evaluation unit is configured to:
    a. define a third signal component A3, and
    b. define the characteristic value K as a function of:
        (1) a signal characteristic determined from the third signal component A3, and
        (2) the signal characteristics of the signal components A1 and A2.

5. The implantable medical device of claim 4 wherein
    a. the third signal component A3 is defined by the activity of the patient, and
    b. the signal characteristic determined therefrom reflects mean patient activity over a predefined time interval.

6. The implantable medical device of claim 4 wherein the evaluation unit is configured to determine the characteristic value K only at times in which the signal characteristic determined from the third signal component A3 lies in a predefined value range.

7. The implantable medical device of claim 6 wherein the third signal component A3 is defined by one or more of:
    a. patient heart rate,
    b. patient blood pressure, and
    c. patient cardiac impedance.

8. The implantable medical device of claim 1 wherein the evaluation unit is configured to also:
    a. derive a heart rate from the signal components A1 and/or A2, and
    b. define the characteristic value K as a function of the signal characteristics and the heart rate.

9. The implantable medical device of claim 1 wherein:
    a. the implantable medical device further includes a blood pressure sensor, and
    b. the evaluation unit is configured to define the characteristic value K as a function of the signal characteristics and an output of the blood pressure sensor.

10. The implantable medical device of claim 1 wherein:
    a. the implantable medical device further includes an impedance sensor, and
    b. the evaluation unit is configured to define the characteristic value K as a function of the signal characteristics and an output of the impedance sensor.

11. The implantable medical device of claim 1 wherein the implantable device is configured to determine at least one of:
    a. frequency, and
    b. amplitude,
    of respiration from the accelerometer output signal.

12. The implantable medical device of claim 1 wherein the implantable medical device:

a. includes a control unit configured to detect arrhythmias in dependence on the characteristic value K, and
b. delivers therapy to the heart in dependence on the detected arrhythmias.

13. The implantable medical device of claim 1 further including a control unit configured to adjust settings of the implantable medical device in dependence on the characteristic value K.

14. The implantable medical device of claim 1 wherein the implantable medical device is a cardiac pacemaker and/or defibrillator/cardioverter.

15. The implantable medical device of claim 1 wherein the acceleration sensor is a 3D accelerometer.

16. The implantable medical device of claim 1 wherein the acceleration sensor is situated within a pulmonary artery.

17. An implantable medical device including:
a. an acceleration sensor configured to generate an accelerometer output signal;
b. an evaluation unit connected thereto, wherein the evaluation unit is configured to:
   (1) define a signal component A1 from the accelerometer output signal, the signal component A1;
      (a) representing characteristics of a right-ventricular contraction of a heart, and
      (b) being dependent on a right-ventricular amplitude occurring within one cardiac cycle;
   (2) define a signal component A2 from the accelerometer output signal, the signal component A2;
      (a) representing characteristics of a left-ventricular contraction of the heart, and
      (b) being dependent on a left-ventricular amplitude occurring within one cardiac cycle; and
   (3) define a characteristic value K from the signal components A1 and A2, the characteristic value K being a ratio of the right-ventricular and left-ventricular amplitudes;
c. a therapy unit configured to deliver therapy to the heart in dependence on the characteristic value K.

18. The implantable medical device of claim 17 wherein the acceleration sensor is situated within a pulmonary artery.

19. The implantable medical device of claim 17 wherein:
a. the evaluation unit is further configured to define a third signal component A3, wherein the third signal component A3 is dependent on the activity of the patient; and
b. the characteristic value K is additionally defined from the third signal component A3.

20. The implantable medical device of claim 19 wherein the characteristic value K is defined only at times in which the third signal component A3 lies in a predefined value range.

21. A method having the steps of:
a. generating an accelerometer output signal,
b. defining at least two signal components A1 and A2 from the accelerometer output signal, wherein:
   i. the signal component A1 is associated with a right-ventricular contraction of a heart, and
   ii. the signal component A2 is associated with a left-ventricular contraction of the heart;
c. determining signal characteristics of each of the signal components A1 and A2 wherein the signal characteristics include amplitudes occurring within one cardiac cycle;
d. defining a characteristic value K from the signal characteristics, wherein the characteristic value K is a ratio of values of the amplitudes; and
e. delivering therapy to the heart in dependence on the characteristic value K.

22. The method of claim 21 wherein the accelerometer output signal is generated from an accelerometer situated in a pulmonary artery.

23. The method of claim 21:
a. further including the step of defining a third signal component A3, wherein the third signal component A3 is dependent on the activity of the patient; and
b. wherein the characteristic value K is further defined from the third signal component A3.

24. The method of claim 23 wherein the characteristic value K is determined only at times in which the third signal component A3 lies in a predefined value range.

25. The method of claim 23 wherein the third signal component A3 is dependent on one or more of:
a. patient heart rate,
b. patient blood pressure, and
c. patient cardiac impedance.

* * * * *